US00PP12390P2

(12) United States Plant Patent
Cosner et al.

(10) Patent No.: US PP12,390 P2
(45) Date of Patent: Feb. 5, 2002

(54) IMPATIENS PLANT NAMED 'TICHER'

(76) Inventors: Harlan B. Cosner; Susan L. Cosner, both of P.O. Box 173, Broadbent, OR (US) 97414

( * ) Notice: Subject to any disclaimer, the term of this patent is extended or adjusted under 35 U.S.C. 154(b) by 0 days.

(21) Appl. No.: 09/535,081

(22) Filed: Mar. 23, 2000

(30) Foreign Application Priority Data

Mar. 30, 1999 (CA) ..... 99-1613

(51) Int. Cl.[7] ..... A01H 5/00
(52) U.S. Cl. ..... Plt./317
(58) Field of Search ..... Plt./317, 319

(56) References Cited

U.S. PATENT DOCUMENTS

PP3,930 P * 6/1976 Hope et al. ..... Plt./317
PP10,260 P * 2/1998 Cosner et al. ..... Plt./317
PP11,487 P * 8/2000 Jonkers ..... Plt./317

OTHER PUBLICATIONS

UPOV–ROM GTITM Computer Database, 2000/06, GTI Jouve Retrieval software, citation for 'TiCher'.*

* cited by examiner

*Primary Examiner*—Bruce R. Campell
*Assistant Examiner*—Susan B. McCormick
(74) *Attorney, Agent, or Firm*—Bradley M. Ganz, Esq.

(57) ABSTRACT

A new and distinct cultivar of *Impatiens walleriana* plant named 'TiCher', characterized by its large cherry red fully double flowers, flowers that are positioned above or beyond the foliage, good heat tolerance, dark green foliage and mounded, freely branching and dense plant habit.

1 Drawing Sheet

BACKGROUND—FIELD OF INVENTION

The present invention relates to a new and distinct cultivar botanically known as *Impatiens walleriana*, and by the cultivar name 'TiCher'.

The cultivar of the accompanying photograph was developed and selected in a controlled breeding program in a controlled environment in Broadbent, Oreg. by the inventors, Harlan Cosner and Sue Cosner, as described herein.

BACKGROUND—DESCRIPTION OF THE PRIOR ART

There are no known commercial cultivars in the prior art having flowers with either a similar or close color.

'TiCher' is a result of a cross between B-9X-31 (the seed parent) and B-9X-3439 (the pollen parent). The above-named parents were semi-double in flower form compared to 'TiCher' which has a fully double flower.

Another difference is the above-named pollen and seed parents of 'TiCher' were capable of sexual reproduction by producing both pollen and seed, compared to 'TiCher' which is both male and female sterile, and the inventors have never seen reproductive organs develop on the flowers of 'TiCher'.

COMPARISON

The impatiens plant of the present invention differs from prior plants, namely Salsa Red U.S. Plant Pat. No. 9,606 in the following ways:

1. The plant of the present invention has been shown to perform better in the heat than Salsa Red; and 2. The adaxial surface of the present invention's flowers is 57A compared to 45A on Salsa Red;

These and other characteristics will be apparent to persons skilled in the art.

BACKGROUND—DISCOVERY AND PARENTAGE

The present cultivar was developed by standard cross-pollination. Its seed parent is a semi-double impatiens plant with large red semi-double flowers. This plant was designated B-9X-31 under the inventors' controlled breeding program. The pollen parent is a semi-double impatiens plant with large cherry red semi-double flowers. This plant was designated B-9X-3439 under the inventors' controlled breeding program. The parent plants are not the subject of any granted patent or pending application. The cross was made in the inventors' controlled breeding program, and the first asexual reproduction was made at Broadbent, Oreg. Successive asexually reproduced generations have shown the present invention to be stable. Each asexually reproduced generation has been accomplished using lateral stems with leaves.

The traits of the cultivar of the present invention that have been observed in each successive generation of asexual reproduction and which are unique are the large cherry red fully double flowers, flowers that are positioned above or beyond the foliage, good heat tolerance, dark green foliage and mounded, freely branching and dense plant habit.

Color references are according to The Royal Horticultural Society Colour Chart, except where general terms of ordinary dictionary significance are used.

DETAILED DESCRIPTION

The following observations, measurements and description of the plants and flowers are based on the environmental and cultural practices at Broadbent, Oreg. The following measurements, values and comparisons describe plants grown under a double layer of polyethylene film with temperatures typically ranging from about 55° F. to about 85° F. during the daytime. Night heat was provided by bench top set at 62° F. The individual plants were grown in six-inch Azalea containers in a soiless medium. Plants were liquid fed with high nitrate plus trace elements applied at N level 150 PPM of two successive feedings followed by one leaching with clear water. Cuttings were stuck in the last week of June and finished in late September. Light levels were between 4,000 and 6,000 ft. candles.

The plant of the present invention has not been observed in all possible environmental and/or cultural conditions. The phenotype may vary significantly with variations in environment such as temperature, light level, humidity and also with cultural practices such as fertility, soil and water quality.

The accompanying photograph illustrates the overall appearance and the flower color of the cultivar of the present invention described herein. The photograph was taken of a mature plant 14 weeks of age during full inflorescence. There may be variations between the colors in the photograph and the colors in the following description due to, for example, light reflectance, or the amount of blue or red light captured in the film. If such variations occur, the written description shall control.

The following description was taken of the 'TiCher' cultivar shown in the photograph.

Parentage: The new cultivar was developed by standard cross-pollination. As noted above, its seed parent was a semi-double with large red flowers; its pollen parent was a semi-double with cherry red colored flowers.

Propagation:

*Type cutting.*—Lateral tips of plants were the cuttings used for asexual reproduction.

*Time to initiate roots.*—Approximately 7 to 14 days at 72° F. soil temperature.

Appearance and form of plant:

*Plant form and habit.*—Mounded with a medium vigorous, dense and bushy growing habit. A free-branching habit.

*Plant size.*—Height is about 27 cm and width is about 42 cm.

*Root description.*—Numerous, fibrous and well-branched roots characterize the rooting habit.

*Branching habit.*—Numerous and self-branching. Stems are strong and freely produced. The number of stems depends upon cultural practices, age of stems used as cuttings and the number of growth buds present on the cutting when stuck. The observed plant's average stem length is about 21 cm. Each stem generally produces about three laterals.

*Stems.*—Diameter is about 0.5 cm. Internode length is about 2.5 cm. Color is 146A with reddish node markings appearing closest to about 187A. These markings appear smaller and less frequent in the internodes. The observed plant's stem texture is smooth.

*Foliage.*—Leaves are slightly quilted, with older leaf edges curving upwardly slightly, alternating along branches. Shape is ovate with acute to acuminate apex, attentuate base and crenate margin. Texture is smooth and satiny. The observed plant's leaf venation pattern is similar to other plants having similar leaf shapes, with single veins branching upwardly off from the central, longitudinal axis of each leaf, along the length of the axis, toward the margin of the leaf and forming an acute angle relative to the axis.

*Foliage size.*—Size of the largest leaves is about 5 cm in length, and 4 cm in width.

*Foliage color.*—Adaxial color is darker than 147A, venation color 147A; abaxial color is 147B with darker markings that are of a difficult to determine color due to a greenish overtone but which appear close to 177A, venation color is close to 146A.

*Petioles.*—Petiole shape is half round with a flat upper surface measuring about 3 mm wide, about 2 mm in depth, and about 2.5 cm in length. Color on the top is hard to determine but appears closest to 148A with reddish markings too small to determine color but which appear close to 178A or 178B. Bottom color is 148A with reddish markings too small to determine color, but appear close to 178A or 178B.

*Flower size.*—Diameter of largest flowers is about 4.8 cm, and depth of about 1.7 cm.

*Flower texture.*—The flower texture is smooth and satiny.

*Flower count.*—Flowers per branch usually number about 15 per branch from visible buds to open flowers at a time throughout the flowering season.

*Flower fragrance.*—No discernible fragrance.

*Natural flowering season.*—Year around under greenhouse conditions, and the frost-free period from spring through fall outdoors.

*Duration of flowering.*—Flowers are produced continuously throughout the growing season.

*Time to flower.*—About six weeks from a rooted cutting.

*Buds.*—Ovate shape with length of about 1 cm, width of about 0.7 cm and depth of about 1 cm. Color of top is 144A, and bottom color is 144B to 144C.

*Petal size and shape.*—Shape is obovate with entire margin, attenuate base, and obtuse to retuse apex. Usually two petals fused at base comprise the largest petals, each being about 2 cm wide and 2.5 cm long.

*Petal color.*—Adaxial surface is 57A; abaxial surface is 57D.

*Petal count.*—Numerous, generally 20 or more.

*Spur.*—Shape is curved acicular tapering tube with length about 3 cm; sepal and width about 2 mm. Color is 146C toward sepal and close to 178A at apex.

*Calyx.*—The calyx consists of a single sepal. The sepal shape is ovate with obtuse base and acute to acuminate apex, and entire margin. Length is about 1 cm and width is about 1 cm. Adaxial color is 142D with purplish spot where the spur attaches close to 57C; abaxial color is 142C to 142D.

*Peduncles.*—Length is about 2.7 cm and diameter is about 2 mm. Color is 146B. Peduncles have a smooth texture.

*Pedicels.*—Usually numbering 2 or 3, each having a length of about 2 cm and diameter of about 1.5 mm. Color is 146B. Pedicels have a smooth texture.

*Reproductive organs.*—The plants of the new cultivar are both male and female sterile. No reproductive organs have been found to exist.

*Heat tolerance.*—Plants of the instant cultivar were grown side by side with 'Salsa Red' in Alva, Fla. in the late spring and summer. The instant cultivar had a more fully double flower than 'Salsa Red', and had a better growth habit than 'Salsa Red' in that 'Salsa Red' did not branch as well, and tended to be a weaker plant.

*Disease resistance.*—The instant cultivar has shown good resistance to botrytis in commercial production.

*Rooting ability.*—Easy, no hormones needed.

What is claimed:

1. A new and distinct cultivar of *Impatiens walleriana* as illustrated and as described herein.

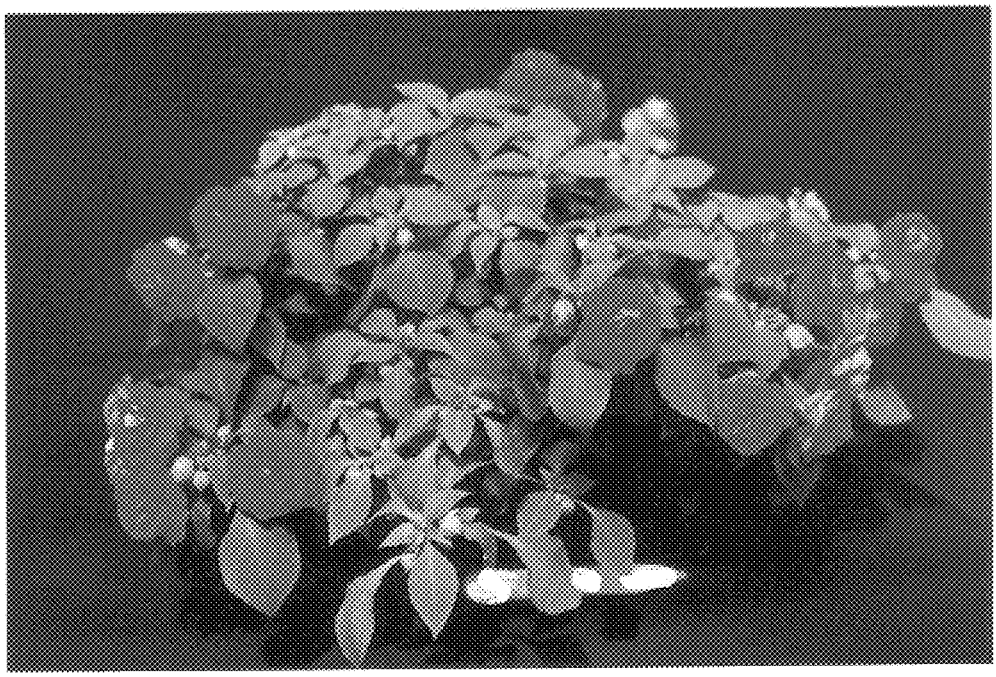

* * * * *